United States Patent [19]
Dempsey et al.

[11] Patent Number: 6,057,758
[45] Date of Patent: May 2, 2000

[54] HANDHELD CLINICAL TERMINAL

[75] Inventors: Michael K Dempsey, Westford; Brian S Rosnov, Wakefield, both of Mass.

[73] Assignee: Hewlett-Packard Company, Palo Alto, Calif.

[21] Appl. No.: 09/081,800

[22] Filed: May 20, 1998

[51] Int. Cl.[7] .............................. G08B 1/08; A61N 1/18
[52] U.S. Cl. ................. 340/539; 340/573.1; 128/903; 607/32; 702/19
[58] Field of Search ................. 340/539, 573.1; 128/903, 904, 697; 607/32; 604/67, 60, 891.1; 702/19

[56] References Cited

U.S. PATENT DOCUMENTS

| | | | |
|---|---|---|---|
| 5,319,355 | 6/1994 | Russek | 340/573 |
| 5,335,664 | 8/1994 | Nagashima | 128/903 |
| 5,417,222 | 5/1995 | Dempsey et al. | 128/696 |
| 5,462,051 | 10/1995 | Oka et al. | 128/904 |
| 5,534,851 | 7/1996 | Russek | 340/573 |
| 5,576,952 | 11/1996 | Stutman et al. | 128/670 |
| 5,689,229 | 11/1997 | Chaco et al. | 340/573 |
| 5,704,351 | 1/1998 | Mortara et al. | 128/904 |
| 5,752,976 | 5/1998 | Duffin et al. | 128/903 |
| 5,827,180 | 10/1998 | Goodman | 600/300 |

OTHER PUBLICATIONS

OpenAir Buyer's Guide, Guide to the WLI Forum, pp. 1–32, Jan. 1997.

*Primary Examiner*—Donnie L. Crosland

[57] ABSTRACT

A system for monitoring a physiological condition of a patient includes a primary station and a portable station. The primary station includes a transmitter configured to transmit a signal, which represents a physiological condition of the patient, via a wireless communication link. The portable station includes: a receiver configured to receive the signal, via the wireless communication link, from the primary station; a display configured to display, based upon the signal, a representation of the physiological condition to a user, and an alarm exhibitor configured to exhibit an alarm indication to the user in response to an identified anomaly in the physiological condition of the patient. The alarm exhibitor may be configured to exhibit the alarm indication in response to an alarm signal received, via the wireless communication link, from the primary station. The portable station may include a transmitter adapted to communicate, via the wireless communication link, with the primary station to permit the user to respond to the alarm indication.

32 Claims, 9 Drawing Sheets

HANDHELD CLINICAL TERMINAL

BACKGROUND OF THE INVENTION

1. Field of the Invention

The present invention is directed to patient monitoring systems.

2. Discussion of the Related Art

A variety of devices currently are used to monitor physiological conditions of patients. For example, bedside monitors, transport monitors and telemetry transmitters are used for this purpose. Data from these devices generally is transferred in "real-time" to a centrally located station, such as a nurse station in a hospital or other medical treatment facility. Electronic equipment at the central station typically processes and displays this data to persons at the central station. In processing the data, the central station commonly uses electronic equipment to analyze the data to identify anomalies in physiological conditions of the patients being monitored. If such an anomaly is identified, then the central station generates an alarm. This alarm may be annunciated at the central station, may be transmitted to a hallway display (described below), or may be transmitted to a device in the possession of one or more clinicians responsible for the patient whose physiological data triggered the alarm.

The electronic equipment at the central station may falsely identify anomalies in the physiological conditions of patients based upon the data received from patient monitoring devices. For example, normal electrocardiograph (ECG) data may cause a central station to generate false alarms. Because some central stations receive data from a very large number of patients (e.g., in large hospitals), it is not uncommon for many false alarms to be generated by a central station over the course of a day.

In many cases, the only way to determine whether the electronic equipment at the central station has properly identified an anomaly in the physiological condition of a patient is for a clinician to examine a displayed version of the data, for example, an ECG activity display. Only after the clinician has reviewed this display can he or she determine with any degree of confidence whether the alarm generated by the central station is valid or invalid.

In some hospitals, a person at the central station determines whether each alarm generated by the central station electronic equipment is valid or invalid. If this person determines an alarm is valid, then he or she notifies the appropriate nurse or physician that one of his or her patients is having difficulty, or notifies others if some other action is required. The person located at the central station therefore must be medically trained. This medically trained person, however, spends none of his or her time actually caring for patients. Maintaining medically trained personnel at a central station for the sole purpose of reviewing patient alarms can impose a significant financial burden on a medical treatment facility.

In other hospitals, due to increasing pressures to minimize costs, it is not always possible to keep a clinician at the central station at all times. Rather, in these hospitals, clinicians are responsible for care giving in addition to recognizing and responding to patient alarms. Therefore, these clinicians become aware of alarms only when they are in the vicinity of the central station. This can cause delays in the acknowledgment of alarms and therefore can cause delays in the treatment of patients with serious conditions.

Additionally, since the central station monitors several patients concurrently, it can alarm quite frequently. These alarms are annunciated loudly, so that they will be noticed promptly by clinicians at or near the central station. As a result, there is a considerable amount of noise in the central station area. This noise can make it difficult to get someone's attention in this area to let them know something is wrong and may be annoying and distracting to persons in the area.

Instead of maintaining clinically trained personnel at the central station at all times, alarm signals generated by the electronic equipment at the central station may be distributed to one or more clinicians responsible for the patient whose data triggered the alarm, and that clinician then may walk to the central station or the patient's bedside (if bedside monitoring is provided) to view a display of the patient's physiological data. One device used to distribute alarm information to clinicians is a so-called "nurse pager." Generally, a nurse pager alerts a clinician that an alarm has activated for a specific patient by providing an alarm indication, such as an audio or vibrational indication, and provides the clinician with textual information regarding the nature of the alarm.

Nurse pagers, however, do not provide real-time waveforms for the clinician to review, so the clinician must walk to the central station or the patient's room in order to accurately determine the validity or invalidity of the alarm. Therefore, in using this alternative, much of the clinician's time and energy is wasted in walking to the central station or the patient's room in order to validate or invalidate alarms. Further, conventional nurse pagers do not provide a bi-directional link between the "pager" and the "pagee," so that the central station is uncertain at any given time whether a clinician has received an alarm and/or whether the clinician has responded to it.

One device used to review physiological data at a patient's bedside is described in U.S. Pat. No. 5,417,222 to Dempsey et al., which is assigned to the assignee of the present application. This device is portable and interfaces with a telemetry unit at a patient's bedside to allow a clinician to view real-time waveforms representative of the physiological condition(s) of the patient. This device, however, does not provide the ability to receive alarm-related information from the central station and does not permit a clinician to validate or invalidate an alarm received by another device, e.g., a pager. Therefore, if a clinician receives an alarm indication from another device, such as a pager, and uses the Dempsey et al. device to view a patient's physiological data to determine the validity of the alarm (after interfacing with a telemetry transmitter at the patient's bedside), then the clinician generally still must walk to or call the central station in order to validate or invalidate the alarm. This can be inconvenient for the clinician and can consume a large amount of the clinician's time.

As a partial solution to this problem, so-called "hallway displays" are used in some medical treatment facilities. Hallway displays are monitors, mounted in a hallway, that can display real-time physiological data and waveforms to physicians. Some hallway displays also provide for two-way communications between the hallway display and the central station, so that a clinician may acknowledge the receipt of an alarm and/or validate or invalidate an alarm from the hallway display. These displays, however, are relatively large and are fixed permanently to the wall or ceiling, so that clinicians still must walk to specific locations in a treatment facility to view the information they need.

Portable devices that display so-called waveform "snippets" also are known. A waveform snippet essentially is a "snapshot" of a waveform that may be analyzed by a clinician to identify characteristics in the waveform that are indicative of certain medical conditions. These devices, however, do not display real-time waveforms to a user, and do not provide for any communications from the user to a central station. Therefore, they do not: (1) allow a user to acknowledge that he or she has received an alarm for a particular patient, or (2) allow a user to validate or invalidate alarms for a patient whose data is being displayed by the device.

U.S. Pat. No. 5,534,851 to Russek describes a system for paging alarms to specific clinicians, together with some textual information about a particular patient. The Russek handheld device, however, does not display real-time waveforms representing a patient's physiological condition(s) to its user. A clinician using this device therefore cannot, in many situations, accurately validate or invalidate alarms using this device.

What is needed, therefore, is an improved device and method for monitoring the physiological conditions of patients.

SUMMARY OF THE INVENTION

According to one aspect of the present invention, a portable device for monitoring a patient includes: a receiver, a display and an alarm exhibitor. The receiver is adapted to receive a signal, which represents a physiological condition of the patient, via a wireless communication link. The display is configured to display, based upon the signal, a real-time representation of the physiological condition to a user. The alarm exhibitor is configured to provide an alarm indication to the user in response to an identified anomaly in the at least one physiological condition of the patient.

According to another aspect of the invention, a portable device for monitoring a physiological condition of a patient includes a receiver, a display, an alarm exhibitor and a transmitter. The receiver is adapted to receive a signal, which represents the physiological condition of the patient, via a wireless communication link. The display is configured to display, based upon the signal, a representation of the physiological condition to a user. The alarm exhibitor is configured to provide an alarm indication to the user in response to an identified anomaly in the physiological condition of the patient. The transmitter is adapted to communicate, via the wireless communication link, with a primary station to permit the user to respond to the alarm indication.

According to another aspect of the present invention, a method for monitoring a patient includes the steps of: (a) using a portable station to receive a signal, which represents a physiological condition of the patient, via a wireless communication link; (b) using the portable station to display, based upon the signal, a real-time representation of the physiological condition to a user; and (c) using the portable station to exhibit an alarm indication to the user in response to an identified anomaly in the physiological condition of the patient.

According to another aspect of the invention, a method for monitoring a patient includes the steps of: (a) using a portable station to receive a signal, which represents a physiological condition of the patient, via a wireless communication link; (b) using the portable station to display, based upon the signal, a representation of the physiological condition to a user; (c) using the portable station to exhibit an alarm indication to the user in response to an identified anomaly in the physiological condition of the patient; and (d) using the portable station to transmit a response to the alarm indication, via the wireless communication link, to a primary station.

BRIEF DESCRIPTION OF THE DRAWINGS

The present invention will be more clearly appreciated from the following detailed description when taken in conjunction with the accompanying drawings, in which like-reference numerals indicate like structures or method steps, and in which the left-most one or two numerals of a reference numeral indicate the number of the figure in which the referenced element first appears, and in which.

DETAILED DESCRIPTION OF THE INVENTION

One embodiment of the present invention includes an improved system for distributing information regarding the physiological conditions of patients from a central station, or from patient monitoring apparatus, to the clinicians responsible for the care of such patients. In such a system, one or more selected real-time waveforms, as well as other patient related information, are transmitted to handheld terminals in the possession of one or more clinicians who are not necessarily located at the central station or in the vicinity of the patient. These real-time waveforms may be displayed by selected ones of the handheld terminals when the selected terminals receive alarm signals from the central station or from the patient monitoring apparatus and provide alarm indications, such as audio or vibrational alarms, to the persons in possession of the terminals. Thus, when a clinician's terminal provides an alarm indication regarding the physiological condition of a particular patient, the clinician may use his or her handheld terminal to view the real-time waveform and/or other patient-related information, and take the appropriate action, instead of having to walk to the central station, the patient's bedside, or a hallway display to view, acknowledge and/or respond to the alarm. Patient specific information, such as real-time waveforms, may also be displayed by handheld terminals in response to requests initiated by clinicians in possession of the terminals.

As used herein, "real-time" is used to describe a representation or measurement of an event or condition that occurs only a short time after the event or condition has taken place. According to one embodiment, a real-time waveform representing a physiological condition of a patient is displayed to a user less than 100 milliseconds after the occurrence of the condition.

According to one embodiment of the invention, the handheld terminal is portable and employs wireless two-way communications. Therefore, the terminal is capable of being powered by batteries and includes circuitry for establishing a wireless two-way communications link with at least one device that generates alarm signals and with at least one device that transmits real-time physiological data, which may be the same or a different device from the device that generates alarm signals. It should be appreciated that appropriate terminals or ports may be provided on the handheld terminal to permit the user of the handheld terminal to interface optionally with an external power source or with an appropriate hardwired communications network.

Figure 1:
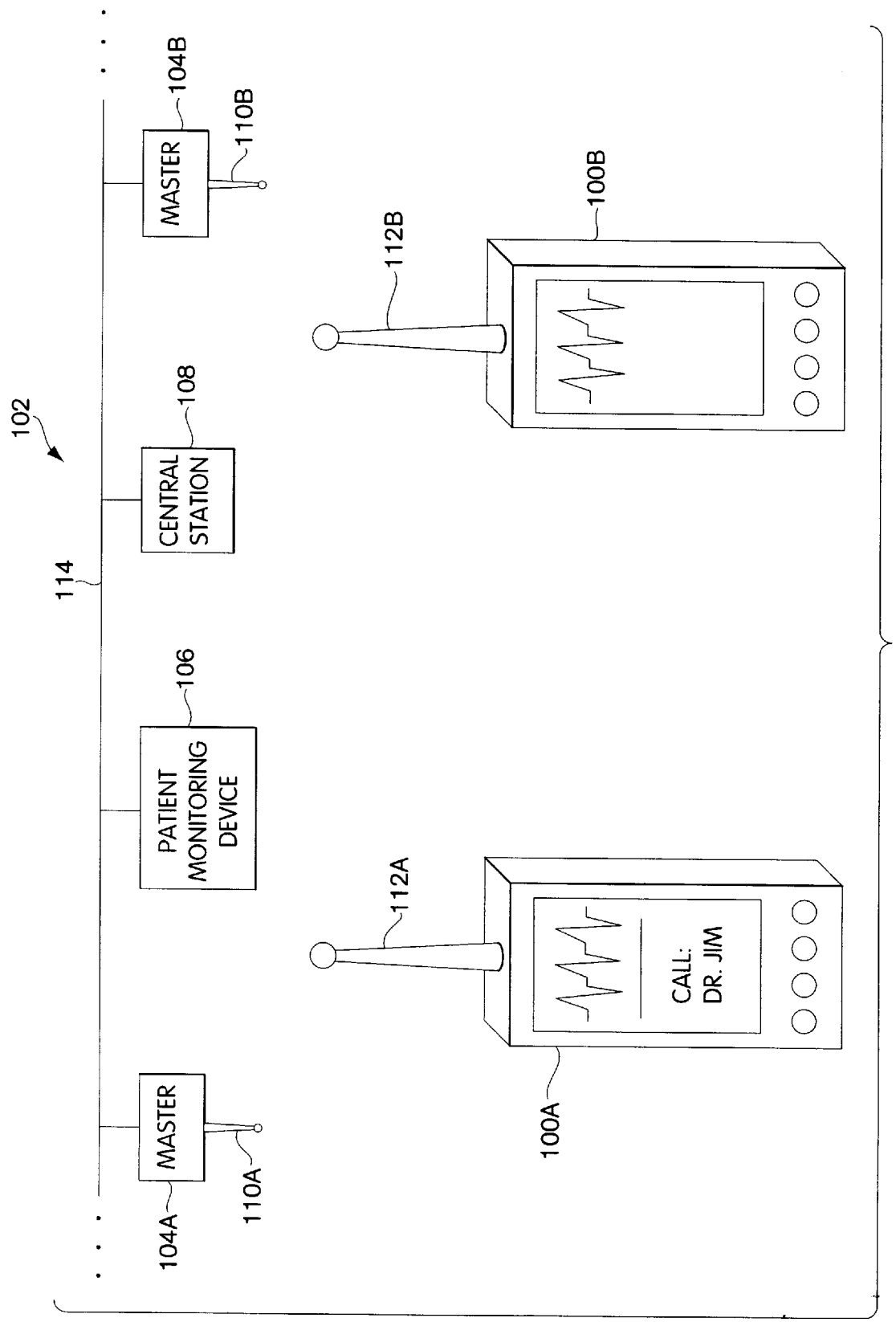
FIG. 1 is a block diagram of a patient monitoring system according to one embodiment of the present invention.

FIG. 1 shows a patient monitoring system configured according to one embodiment of the present invention. As shown, the system includes a patient monitoring device 106, a central station 108, and two handheld clinical terminals 100A and 100B These devices are interconnected using a local area network (LAN) 102, including master cell controllers 104A and 104B connected to a backbone 114, i.e., a hardwired network, such as a 10BaseT backbone. Master cell controllers 104A and 104B permit portable devices, such as handheld terminals 100A and 100B to be included on LAN 102. Master cell controllers 104A and 104B and handheld terminals 100A and 100B include antennas 110A, 110B, 112A and 112B, respectively, to transmit and receive signals between one another. Each of master cell controllers 104A and 104B includes circuitry for transmitting and receiving signals via antennas 110A and 110B, respectively, within respective "cells" of the physical area in which wireless communication is desired. Additionally, each of handheld terminals 100A and 100B includes circuitry for transmitting and receiving signals via antennas 112A and 112B, respectively.

It should be appreciated that in an actual implementation of this embodiment of the invention: (1) additional patient monitoring devices may be provided to monitor additional patients, (2) additional master cell controllers may be supplied to ensure that wireless signals from LAN 102 are transmitted and received from every area of a treatment facility within which wireless communication on LAN 102 is desired, and (3) additional handheld clinical terminals may be provided so that each clinician may have such a terminal in his or her possession.

Figure 2:
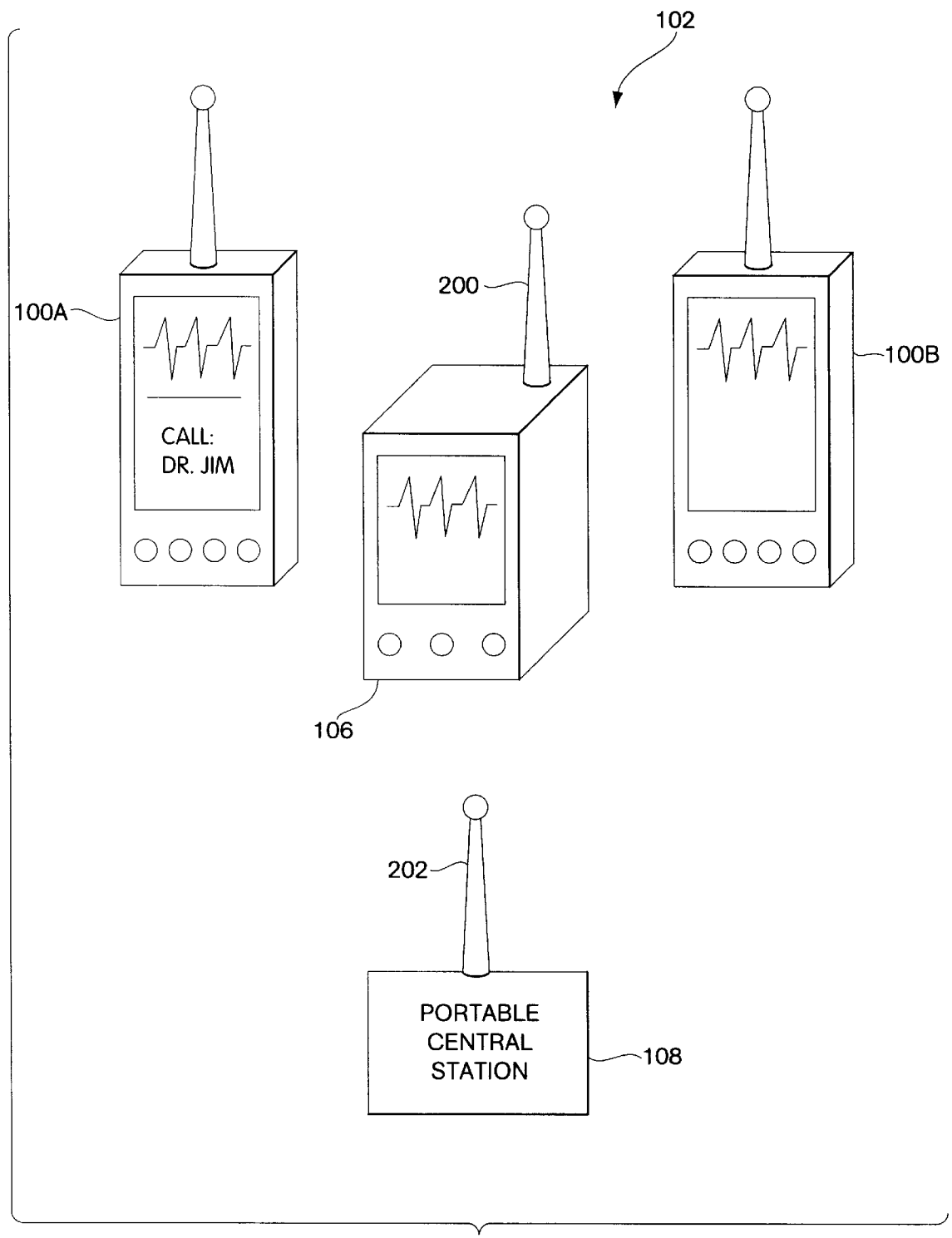
FIG. 2 is a block diagram of a patient monitoring system according to another embodiment of the invention.

FIG. 2 shows another embodiment of a patient monitoring system interconnected on LAN 102 according to the invention. As shown, according to this embodiment, each of patient monitoring device 106, central station 108, and handheld terminals 100A and 100B includes an antenna (i.e., antennas 200, 202, 112A and 112B, respectively) to communicate with the other devices included on LAN 102. The system shown in FIG. 2 therefore includes the same network elements as the system shown in FIG. 1, but does not require backbone 114 for communication between central station 108 and patient monitoring device 106. It should be appreciated that any of these elements also may include a communications port by which it may be connected to a backbone having master cell controllers connected to it for increased reliability when such a backbone is available.

In either of the embodiments shown in FIGS. 1 and 2, each message transmitted by one of the elements on LAN 102, e.g., by patient monitoring device 106, central station 108, or either of handheld clinical terminals 100A and 100B, includes a unique identifier, e.g., a Transmission Control Protocol/Internet Protocol (TCP/IP) or Media Access Control (MAC) address, that identifies at least one network element for which the message is intended.

Patient monitoring device 106 may include any device capable of placing data regarding one or more physiological conditions of a patient onto LAN 102. Device 106 therefore may include, for example, a bedside patient monitor, a transport monitor, or a telemetry-type patient monitor.

According to one embodiment, central station 108 receives data from patient monitoring device 106 via LAN 102, as well as from several other patient monitoring devices included on LAN 102. Central station 108 preferably is centrally located in the medical care facility, e.g., at a centrally located nurse station, so as to permit medical personnel at the station to respond quickly to alarms generated in response to the detection of anomalies in the physiological data from various patients.

In response to a sensed anomaly in the physiological condition of a patient, central station 108 may transmit an alarm signal to one or more selected handheld terminals, e.g., handheld terminals 100A or 100B, via LAN 102. Alternatively, each patient monitoring device, e.g., patient monitoring device 106, may itself process and analyze a patient's physiological data and generate alarm signals in response to sensed anomalies in such data. Patient monitoring device 106 therefore may also transmit alarm signals to one or more selected handheld terminals via LAN 102. In addition to such an alarm indication, central station 108 or patient monitoring device 106 also may transmit one or more real-time waveforms representing physiological condition(s) of a patient to these selected handheld terminals.

According to this embodiment, patient monitoring device 106 and/or central station 108 is capable of sourcing real-time waveforms and alarm data to specific devices on LAN 102. One way that this may be accomplished is through a server, such as a Java™ server, available from Sun Microsystems, Inc. (Java is a trademark of Sun Microsystems, Inc.). A given patient monitoring device 106 (which is identified on the network through, for example, a MAC address or a TCP/IP address) may be bound to one or more handheld terminals (which are identified in a similar manner). This binding may be initiated automatically by the system or manually at patient monitoring device 106, at central station 108, or at each of handheld terminals 100A or 100B.

When an alarm is generated for a particular patient, patient monitoring device 106 or central station 108 may send a message to the clinician who is bound to that patient. A real-time communications channel on network 102 may be opened between patient monitoring device 106 or central station 108 and one or more of handheld terminals 100A and 100B. Patient monitoring device 106 or central station 108 then may send a Java applett to the selected handheld clinical terminal(s) and begin to stream waveform data to that applett. The clinician then may review this real-time waveform and make a determination as to the appropriate response. This response then may be sent back to patient monitoring device 106 or central station 108 and appropriate action may be taken. According to one embodiment, patient-related information is provided to clinicians in less than 100 milliseconds from the time the data is acquired from the patient.

Central station 108 and/or patient monitoring device 106 also may generate and transmit other messages, such as pages, audio transmissions or a video transmissions, to one or more devices included on LAN 102, e.g., one or more selected handheld terminals, using a similar scheme wherein unique identifiers such as TCP/IP or MAC addresses are used to address messages to particular devices.

Each of handheld terminals 100A and 100B continuously monitors the airwaves for messages from patient monitoring devices, e.g., patient monitoring device 106, another handheld terminal, or central station 108. In addition, each handheld clinical terminal may initiate communications with other devices included on LAN 102, for example, each handheld terminal may: (1) page central station 108, patient monitoring device 106 and/or one or more other handheld terminals; (2) initiate audio communication with central station 108, patient monitoring device 106 and/or one or more other handheld terminals; (3) request information on a particular patient that is being monitored by the system; and/or (4) acknowledge or respond to pages or alarms received by it.

Figure 3:
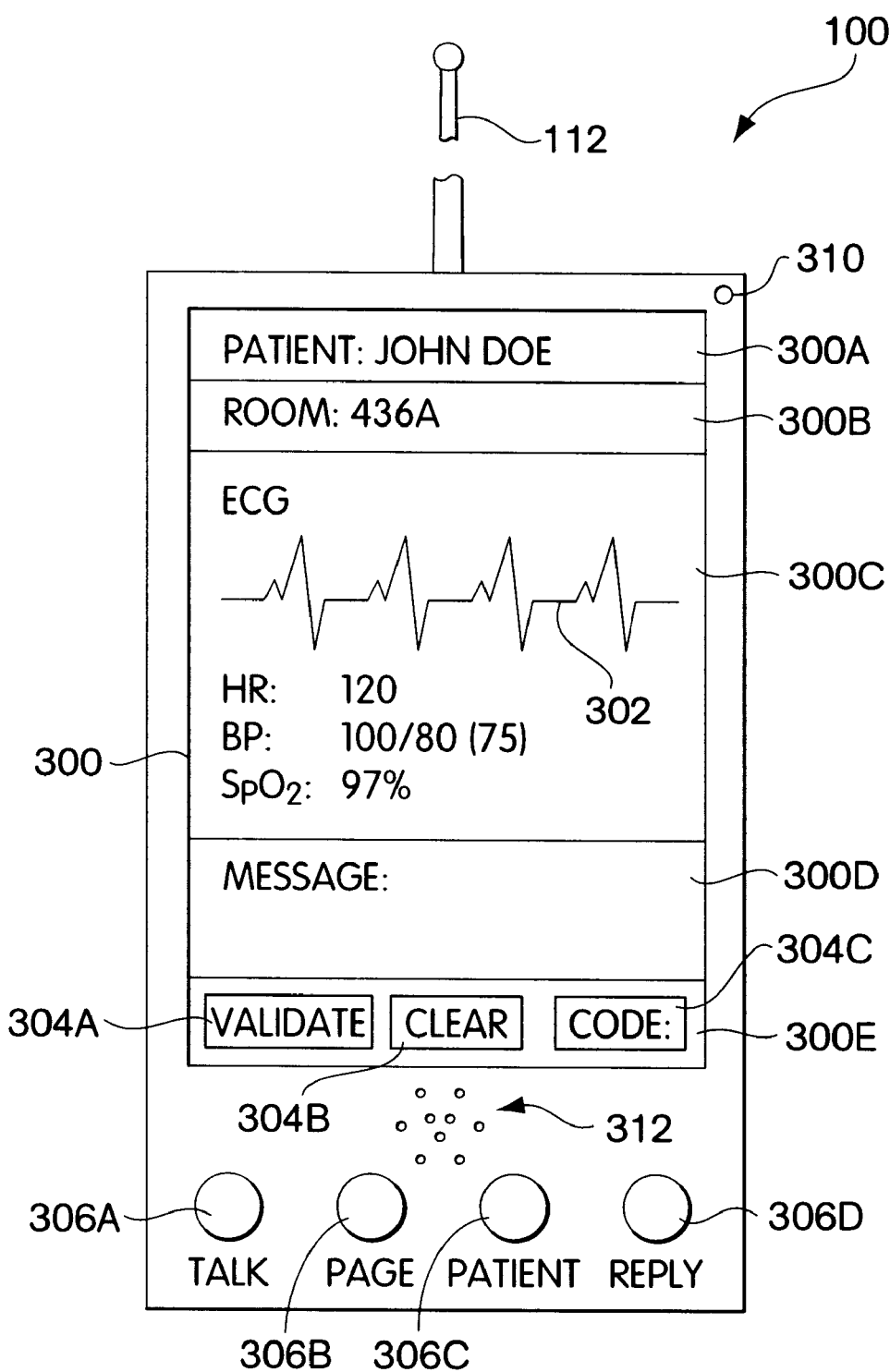
FIG. 3 is a simplified pictorial illustration of a hand-held clinical terminal according to one embodiment of the invention.

FIG. 3 shows an embodiment of a handheld clinical terminal 100 according to one embodiment of the present invention. Handheld terminal 100, which may, for example, be approximately six inches tall, four inches wide, and one-half inch deep, includes a display 300 including five distinct display areas 300A, 300B, 300C, 300D and 300E, four "hard" buttons 306A, 306B, 306C and 306D, a microphone 310, and a speaker 312. Terminal 100 therefore may easily be carried by a user for extended periods, for example, in a pocket. According to one embodiment, display 300 includes at least one touch sensitive part (i.e., a touchscreen) 300E on which various "soft" buttons may be displayed, depending on the current application being run by software internal to handheld terminal 100. It should be understood that the various buttons shown in FIG. 3 and described herein are only examples of buttons that may be provided on handheld terminal 100 and that any other types of buttons, which may perform similar or different functions, may alternatively be employed. Further, it should be appreciated that some of the components of handheld terminal 100 may be interfaceable with the other components via wireless communications links, or may be selectively interfaceable with the other components via terminals or jacks so that, for example, microphone 310 and/or speaker 312 may be physically separate (or separable) from the other components shown in FIG. 3. For example, microphone 310 and speaker 312 may together form a headset that may be worn by the user.

In the example shown in FIG. 3, handheld terminal 100 is shown as it may appear upon receiving an alarm signal from central station 108 or patient monitoring device 106. The clinician using the terminal may respond to this alarm signal by touching one of the soft buttons appearing on area 300E of display 300. That is, the user may: (1) validate the alarm by touching a "validate" button appearing in portion 304A of display area 300E, (2) clear the alarm by touching a "clear" button appearing in portion 304B of display area 300E, or (3) indicate that a "code" condition exists by touching a "code" button appearing in portion 304C of display area 300E. In response to one of portions 304A, 304B, and 304C being touched by the user, handheld terminal 100 may transmit the selected response back to central station 108 or patient monitoring device 106.

As illustrated in FIG. 3, when handheld clinical terminal 100 receives an alarm signal, other patient specific information also may appear on display 300. For example, in the embodiment shown in FIG. 3, the patient's name may appear in display area 300A, the patient's room number may appear in display area 300B, and various real-time patient-related data may appear in area 300C of display 300. The real-time patient-specific data displayed in area 300C may include, for example, a real-time ECG waveform 302, a current heart rate measurement, a current blood pressure measurement, and a current blood oxygenation ($SpO_2$) measurement. Finally, display area 300D may display messages from any other device on LAN 102.

When handheld clinical terminal 100 receives an incoming "page" message, display 300 may display different information to the user and may provide different soft buttons on the touch sensitive portion of display 300. For example, area 300E may display soft buttons permitting the user to: "return," "store," or "delete" a received page message.

Similarly, when handheld clinical terminal 100 receives an incoming audio message, display 300 may display different information to the user and may provide different soft buttons on the touch sensitive portion of display 300. For example, soft buttons may be provided permitting the user to conference the message to other handheld devices, place incoming callers on hold, or mute outgoing voice communications from handheld terminal 100.

The user additionally may page other devices included on LAN 102 by pressing button 306B. For example, when a user presses button 306B, a list of "pageable" devices included on LAN 102 may appear on a touch-sensitive portion of display 300. The user then may scroll through the names or device identifiers appearing on display 300 and (using the touch screen) may select one or more of them to be recipients of a page message.

The user of handheld terminal 100 also may initiate audio communication with another device on LAN 102 by pressing button 306A and speaking into microphone 310, and may hear incoming audio messages from the other devices included on LAN 102 via speaker 312. A recipient of this audio message may be determined in a manner similar to that used to select a recipient of a page message, i.e., by scrolling through names or device identifiers and selecting one or more of them as recipients of the message. When handheld terminal 100 receives an incoming audio message, the user may press button 306A to automatically cause the originator of the message to be selected as the recipient of any responsive message, or optionally the user may select different recipients.

The user additionally may request information regarding a particular patient by pressing button 306C. The user may select a particular patient's information by scrolling through a list of names that appears when button 306C is pushed. By selecting one of these names, an appropriate message may be sent to patient monitoring device 106 or central station 108, and that device, in response, may transmit the requested patient-specific information to the handheld terminal 100 that requested it. Alternatively, patient monitoring device 106 or central station 108 may continuously transmit each patient's information onto LAN 102, regardless of whether such a request has been made, and by pressing button 306C and selecting a particular patient's name, handheld clinical terminal 100 may select one patient's information to be displayed.

The user also may reply to incoming messages by pressing button 306D. Reply button 306D may be used in lieu of the soft buttons appearing on display 300 to respond to incoming messages, or may have a different function from the soft buttons. For example, reply button 306D may cause various soft buttons to appear, or may cause a list of possible recipients of a "reply" message to appear on the touch sensitive portion of display 300 in a manner similar to that in which recipient lists of page messages and voice communications are provided to a user.

Examples of hardware and software that may be used to operate handheld terminal 100 are described below. In addition, other examples are given of information that may appear in the various display areas of display 300 when different functions are performed by the terminal.

Figure 4:
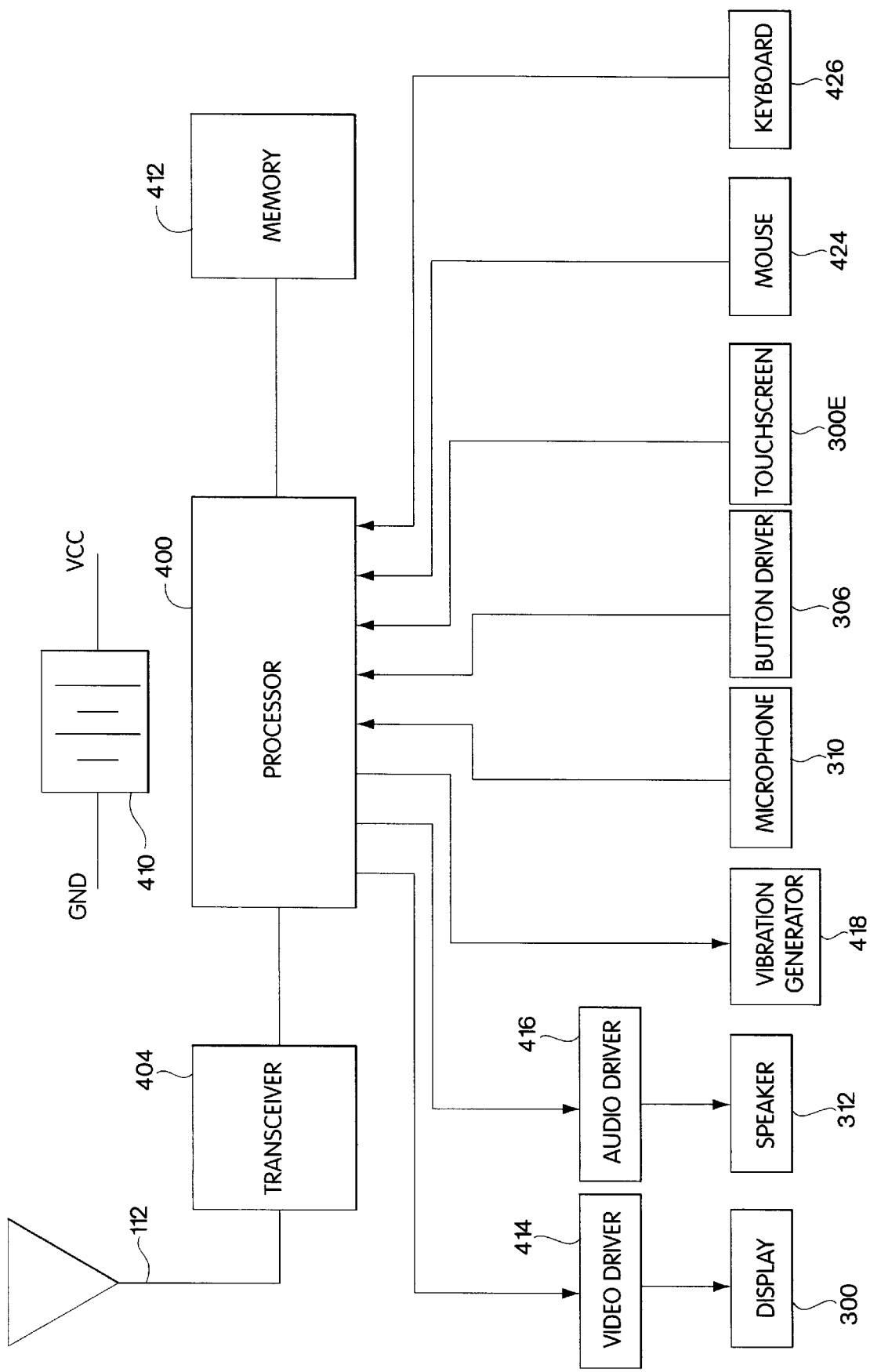
FIG. 4 is a block diagram of hardware components that may be used to implement an embodiment of the hand-held clinical terminal shown in FIG. 3.

FIG. 4 shows hardware components that may be used according to one embodiment of the invention. Several of these components may be included, for example, in a WinCE palmtop device (such as model number HP320LX, manufactured by Hewlett-Packard Company). If such a device is used, then LAN 102 (shown in FIG. 1) may include, for example, a two-way wireless LAN network such as the model RangeLAN II, manufactured by Proxim, Inc.

As shown in FIG. 4, the hardware components of each handheld terminal 100 may include a processor 400 and a memory 412 coupled to processor 400. Memory 412 includes instructions that, when executed by processor 400, cause processor 400 to perform various routines according to different aspects of the invention. Processor 400 may interface with other elements on LAN 102 via transceiver 404 and antenna 112. Transceiver 404 may be any device capable of interfacing an input/output (I/O) handler of processor 400 with a wireless portion of LAN 102. Processor 400, transceiver 404, and all other power consuming devices within each handheld terminal 100 may be powered by one or more batteries 410.

Processor 400 may be coupled to devices that establish an interface with the user of handheld terminal 100. According to the embodiment shown in FIG. 4, a display 300 (driven by a video driver 414), a speaker 312 (driven by an audio driver 416) and a vibration generator 418, all may be provided to output information from processor 400 to the user. To permit the user to input information to processor 400, handheld terminal 100 may include a microphone 310, a button driver 306, and one or more of a touchscreen 300E, a mouse 424 and a keyboard 426. A bar-code scanner (not shown) may also be used to input information to processor 400.

When a message, e.g., an alarm, a page, an audio message, or a video message, is received from LAN 102, the user may be alerted to this fact by one or more of the output devices shown in FIG. 4, i.e., display 300, speaker 312 and/or vibration generator 418, providing an indication to the user that such a message has been received. For example, in response to an alarm signal addressed to the handheld terminal 100, display 300 may provide a video display to the user, speaker 312 may provide an audio signal to the user, e.g., a beeping sound, or vibration generator 418 may cause handheld terminal 100 to vibrate in order to provide an alarm indication to the user.

Each of the user input devices, i.e., microphone 310, button driver 306, touchscreen 300E, mouse 424 and keyboard 426, provides digital data to processor 400 in response to the use of these devices. For example, microphone 310 may include an amplifier and an analog-to-digital converter (ADC) to provide a digital representation of the user's voice to processor 400. Button driver 306 may include circuitry for converting the depression of any of hard buttons 306A, 306B, 306C or 306D to digital signals that indicate to processor 400 that such buttons have been pushed.

Touchscreen 300E and/or mouse 424 may be used to permit the user to select particular soft buttons displayed on display 300. Keyboard 426 may permit a user to provide a digital representation of specific textual information to processor 400. This textual information may be used, for example, to select recipients of messages, to respond to messages, or to perform any other function wherein the user desires to communicate with other devices on LAN 102 or with processor 400 in a manner not provided for by the hard or soft buttons on handheld terminal 100.

According to one embodiment, an I/O handler of processor 400 manages data that is transferred between processor 400 and each of transceiver 404, display 300, speaker 312, vibration generator 418, microphone 310, button driver 306, touchscreen 300E, mouse 424 and keyboard 426. Messages that are received by processor 400 from transceiver 404 may be analyzed by processor 400 to identify whether they include a unique identifier, e.g., a TCP/IP or MAC address, which specifies that handheld terminal. Any messages that are addressed to handheld terminal 100 may be written into one of several buffers, depending on what type of messages they are. Each message received by processor 400 may include information that identifies it as being a particular type of message, e.g., an alarm, page, audio, video, or general purpose message. Messages from processor 400 that are to be transmitted by transceiver 404 also may be written into at least one buffer prior to being retrieved by the I/O handler of processor 400 and transmitted onto LAN 102 by transceiver 404.

Figure 5:
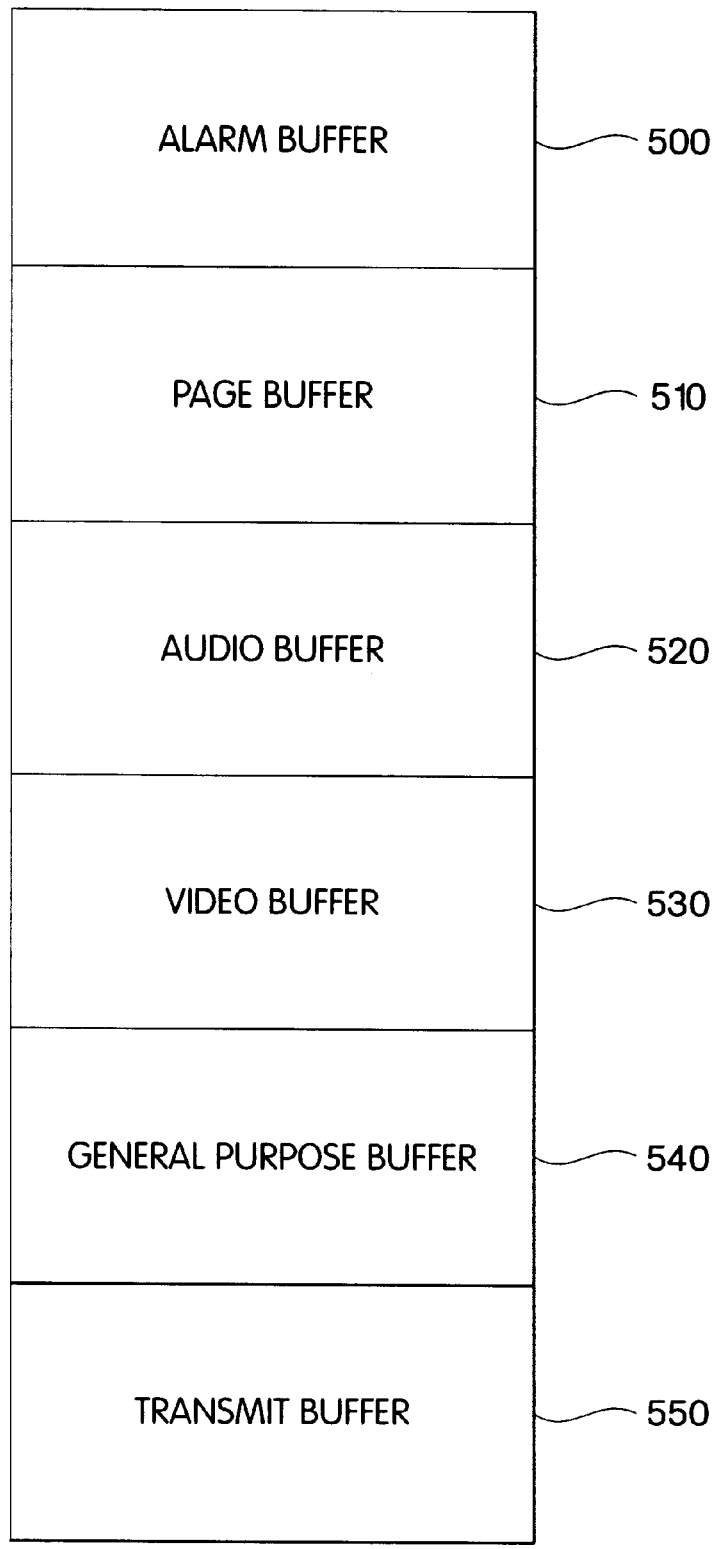
FIG. 5 is a block diagram of several buffers that may be used by an input/output (I/O) handler of the processor shown in FIG. 4.

An example of these buffers is shown in FIG. 5. Five separate buffers, i.e., alarm buffer 500, page buffer 510, audio buffer 520, video buffer 530 and general purpose buffer 540 may be provided to store each of the different types of messages received from LAN 102 that are addressed to handheld terminal 100. Additionally, transmit buffer 550 may be provided to store messages that are to be transmitted by handheld terminal 100 onto LAN 102.

As noted above, processor 400 executes instructions, i.e., software routines, that cause processor 400 to perform operations according to various aspects of the invention. The software stored in memory 412 may be, for example, a Java Virtual Machine™ engine (an object-oriented programming language which may be executed and/or downloaded over a network), available from Sun Microsystems, Inc., or any commercially available browser, such as the Internet Explorer, from Microsoft Corporation (Java Virtual Machine is a trademark of Sun Microsystems, Inc.).

Figure 6:
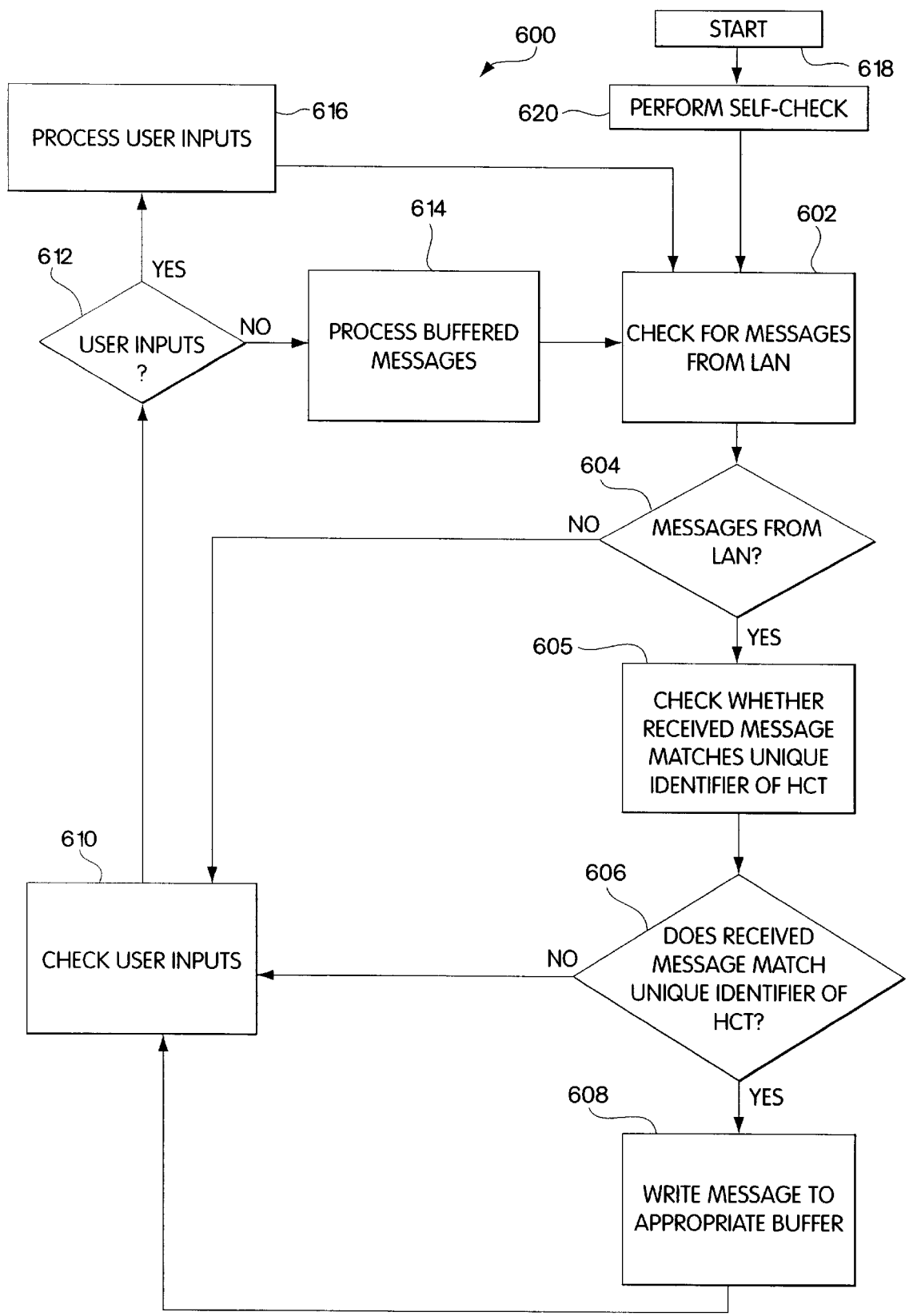
FIG. 6 is a flow chart of a software routine that may be executed by the processor shown in FIG. 4 according to one embodiment of the invention.

FIG. 6 shows an example of a software routine 600 that may be stored in memory 412 and executed by the processor 400 according to one embodiment of the invention. As shown, routine 600 starts at step 618. Step 618 is reached, for example, when a switch is toggled that causes processor 400 to receive power. After step 618, the routine proceeds to step 620, wherein a self-check routine (not illustrated) is performed to ensure that processor 400 and its associated circuitry are operating properly.

After step 618 is completed, routine 600 enters the primary operating routine of processor 400, during which: (a) incoming messages are filtered and placed into appropriate ones of buffers 500, 510, 520, 530 and 540; (b) inputs from the user input devices shown in FIG. 4, i.e., microphone 310, button driver 306, touchscreen 300E, mouse 424, and keyboard 426, are identified, processed and transmitted as needed; and (c) messages placed in buffers 500, 510, 520, 530 and 540 are processed and communicated to the user via the user output devices shown in FIG. 4, i.e., display 300, speaker 312 and vibration generator 418.

In step 602, routine 600 checks to see whether any messages have been received by transceiver 404 from LAN 102, and proceeds to decision step 604. According to decision step 604, if a message has been received from LAN 102, the routine proceeds to step 605, and if a message has not been received from LAN 102, the routine proceeds to step 610.

In step 605, the message received from LAN 102 is examined to determine whether the message includes an identifier that matches the unique identifier of handheld terminal 100, e.g., its TCP/IP or MAC address included in the message is examined to see whether it matches the TCP/IP or MAC address of handheld terminal 100. The routine then proceeds to decision step 606. According to decision step 606, if the identifier in the message matches the unique identifier of handheld terminal 100, the routine proceeds to step 608, and if the identifier in the message does not match the unique identifier of handheld terminal 100, the routine proceeds to step 610.

In step 608, information in the message is examined to determine whether the message is an alarm message, a page message, an audio message, a video message, or a general purpose message, and the message is written to an appropriate one of buffers 500, 510, 520, 530 and 540 (FIG. 5).

In step 610, routine 600 checks for inputs from a user input device, e.g., microphone 310, button driver 306, touchscreen 300E, mouse 424, or keyboard 426, and proceeds to decision step 612. According to decision step 612, if the user has entered an input, the routine proceeds to step 616, and if the user has not entered any inputs that need to be processed, the routine proceeds to process 614.

In step 616, any user inputs are processed and, if appropriate, messages from the user, or responses to messages from other devices on LAN 102, that are waiting in buffer 550 are transmitted onto LAN 102 via transceiver 404. As discussed above, these messages may include page messages and audio messages addressed to other devices on LAN 102, as well as responses to alarms, pages and other messages from other devices on LAN 102.

Figure 7:
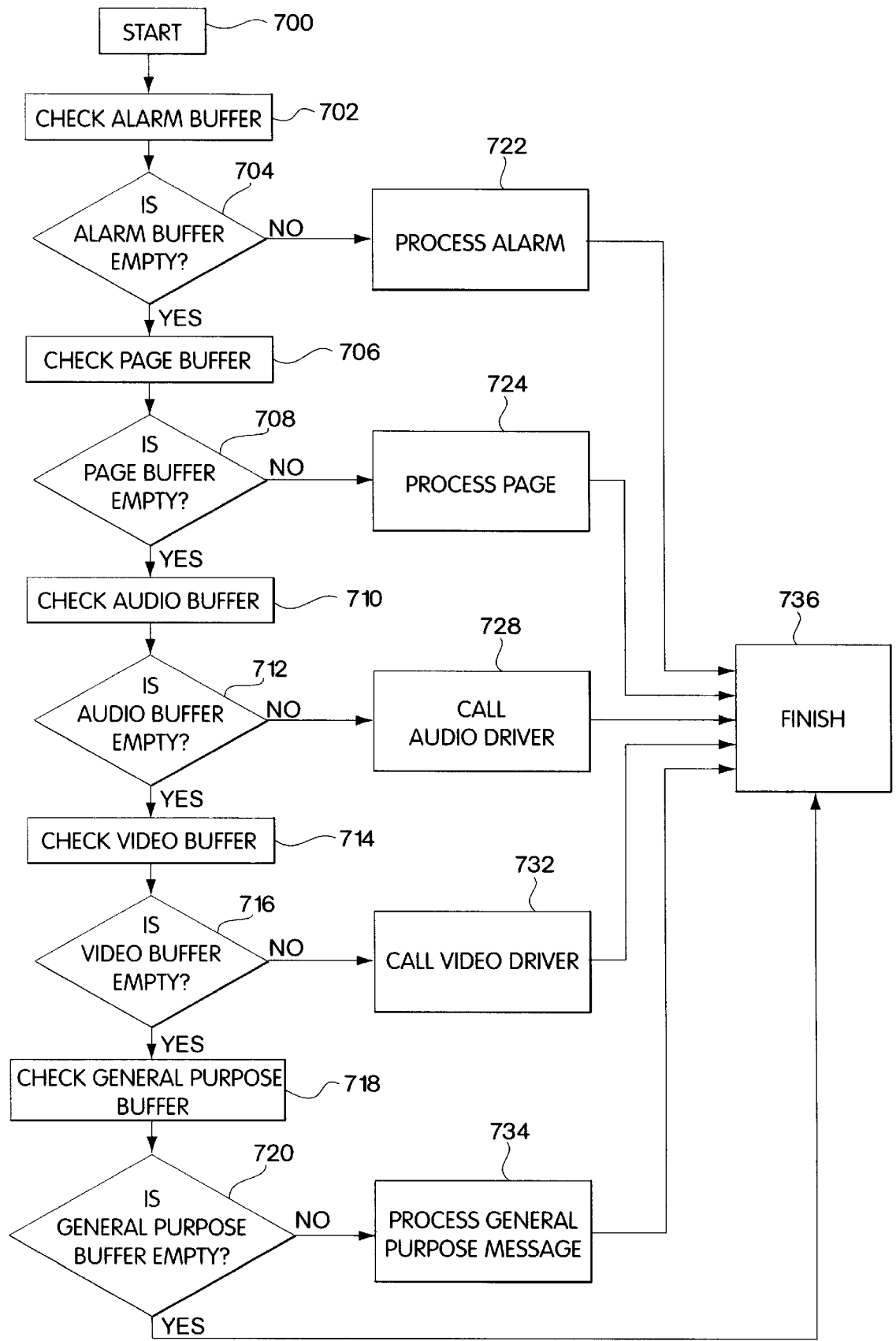
FIG. 7 shows the "process buffered messages" step of the routine shown in FIG. 6 in more detail.

In process 614, which is described in more detail below, any received messages that are waiting in message buffers 500, 510, 520, 530 and 540 are processed. These messages are processed according to a predetermined priority scheme. According to an exemplary embodiment, alarm messages are given the highest priority, followed by page messages, then audio messages, then video messages, and finally general purpose messages. Messages from the same priority level are processed in the same order that they are received. Thus, in this exemplary embodiment, if two or more messages of the same priority level are waiting in one of buffers 500, 510, 520, 530 and 540, the most recently received message is processed first. FIG. 7 shows process 614 in more detail. As shown, process 614 starts at step 700, and immediately proceeds to step 702. In step 702, alarm buffer 500 is checked to determine whether any alarm messages are waiting to be processed, and process 614 then proceeds to decision step 704. According to decision step 704, if any alarm messages are waiting in alarm buffer 500, process 614 proceeds to process 722, and if alarm buffer 500 is empty, process 614 proceeds to step 706.

In process 722 of process 614, an alarm message waiting in alarm buffer 500 is processed. Process 722, which is described in more detail below, is responsible for: (1) providing an alarm indication to the user of handheld terminal 100 in response to receiving an alarm signal; (2) displaying information regarding the patient for which the alarm signal is being generated, e.g., the patient's name, room number, reason for the alarm, etc.; (3) displaying dynamically changing information, including a real-time waveform representative of a physiological condition of the patient; (4) prompting the user for a response to the alarm message; and (5) waiting for a predetermined period of time for the user to respond to the alarm and, after which time, if the user has not yet responded, returning a "timed out" response to the device that generated the alarm so that the alarm may be re-transmitted to another device, e.g., another handheld terminal. After process 722 is completed, process 614 finishes at step 736, and routine 600 (FIG. 6) proceeds to step 602.

In step 706, page buffer 510 is checked to determine whether any page messages are waiting to be processed, and process 614 then proceeds to decision step 708. According to decision step 708, if any page messages are waiting in page buffer 510, process 614 proceeds to step 724, and if page buffer 510 is empty, process 614 proceeds to step 710.

In process 724, a page message in page buffer 510 is processed. Process 724, which is described in more detail below, is responsible for: (1) generating an indication, e.g., a beep or vibration, to the user that a page message has been received, (2) displaying the page message to the user, (3) prompting the user for a response to the page message, and (4) saving the message so that the user may review and respond to the message at another time. After process 724 is completed, process 614 finishes at step 736, and routine 600 (FIG. 6) proceeds to step 602.

In step 710, audio buffer 520 is checked to determine whether any audio messages are waiting to be processed, and process 614 then proceeds to decision step 712. According to decision step 712, if any audio messages are waiting in audio buffer 520, process 614 proceeds to step 728, and if audio buffer 520 is empty, process 614 proceeds to step 714.

In step 728, audio driver 416 (FIG. 4) of handheld terminal 100 is called to output an audio message waiting in audio buffer 520. After step 728 is completed, process 614 finishes at step 736, and routine 600 (FIG. 6) proceeds to step 602.

In step 714, video buffer 530 is checked to determine whether any video messages are waiting to be processed, and process 614 then proceeds to decision step 716. According to decision step 716, if any video messages are waiting in video buffer 530, process 614 proceeds to step 732, and if video buffer 530 is empty, process 614 proceeds to step 718.

In step 732, video driver 414 (FIG. 4) of handheld terminal 100 is called to output a video message waiting in video buffer 530. After step 732 is completed, process 614 finishes at step 736, and routine 600 (FIG. 6) proceeds to step 602.

In step 718, general-purpose buffer 540 is checked to determine whether any general-purpose messages are waiting to be processed, and process 614 then proceeds to decision step 720. According to decision step 720, if any general-purpose messages are waiting in general-purpose buffer 540, process 614 proceeds to step 734, and if general-purpose buffer 540 is empty, process 614 proceeds to step 736.

In step 734, a general purpose message waiting in general purpose buffer 540 is processed. After step 734 is completed, process 614 finishes at step 736, and routine 600 (FIG. 6) proceeds to step 602.

Figure 8:
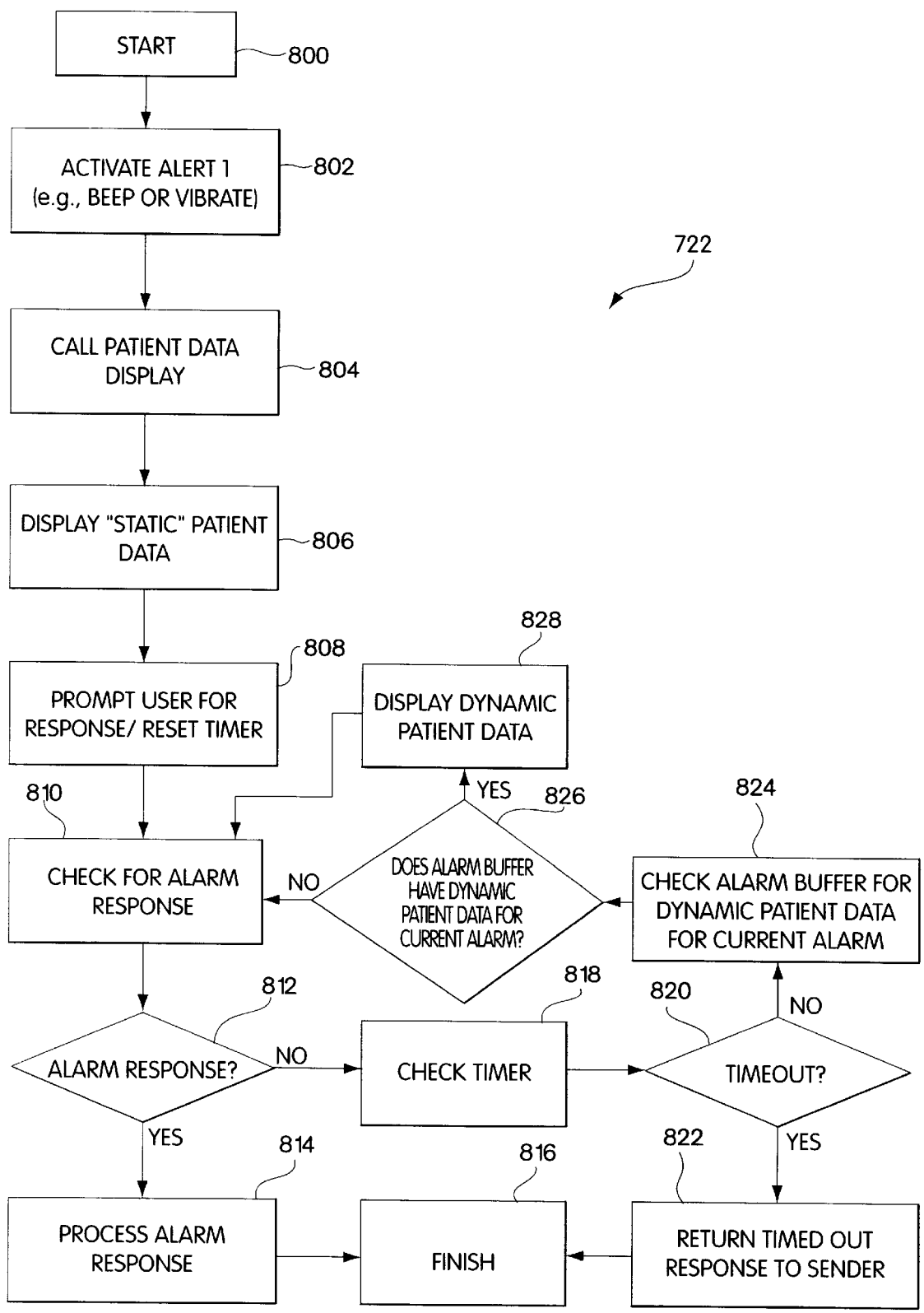
FIG. 8 shows the "process alarm" step shown in FIG. 7 in more detail.

FIG. 8 shows process 722 of process 614 in more detail. As shown, process 722 begins at step 800 and proceeds immediately to step 802, wherein an alarm indication is generated and is provided to the user to alert the user that an alarm message has been received. After completing step 802, the routine proceeds to step 804, wherein a patient data display screen is called and is displayed. The patient data display may include, for example, the features shown on display 300 in FIG. 3. After step 804 is completed, process 722 proceeds to step 806.

In step 806, "static" patient data is displayed on the patient data display screen called in step 804. Static patient data refers to patient-specific data that does not change over time. For example, a patient's name and room number may be considered to be static patient data. After step 806 is completed, process 722 proceeds to step 808.

In step 808, the user is prompted for a response to the received alarm and a timer is reset. This timer is used to identify a "timeout" condition if the user does not respond to the alarm within a predetermined period of time, e.g., thirty seconds. The user may be prompted for a response to the alarm, for example, by the displaying of soft buttons 304A–304C shown in FIG. 3, which permit the user to "validate," "clear," or "code!" the received alarm. After step 808 is completed, process 722 proceeds to step 810, wherein process 722 checks to determine whether the user has input a response to the received alarm.

According to decision step 812, if the user has input a response, for example, by activating a displayed touch-sensitive soft button on display area 300E (FIG. 3), process 722 proceeds to step 814, wherein the user's alarm response is processed. After step 814 is completed, process 722 finishes at step 816, and process 614 (FIG. 7) proceeds to step 736. If, according to decision step 814, the user has not input a response to the received alarm, then process 722 proceeds to step 818, wherein the timer is checked to determine whether more than a predetermined amount of time, e.g., one minute, has elapsed since the user received the alarm.

According to decision step 820, if more than the predetermined amount of time has elapsed, then process 722 proceeds to step 822, wherein an appropriate message is generated and transmitted to indicate that the user has failed to respond to the received message within the predetermined time period. After step 822 is completed, process 722 finishes at step 816, and process 614 (FIG. 7) proceeds to step 736. If, according to decision step 820, the predetermined time period has not yet elapsed, process 722 proceeds to step 824, wherein alarm buffer 500 is checked to determine whether it contains any "dynamic" patient data related to the alarm currently being processed. Dynamic patient data refers to patient-specific data that changes over time. This dynamic data may include, for example, a digital representation of a real-time waveform, or other real-time (or near real-time) information, representing one or more physiological conditions of a patient.

According to decision step 826, if alarm buffer 500 contains dynamic patient data, then process 722 proceeds to step 828, wherein such data is displayed. After step 828 is completed, process 722 proceeds to step 810 (described above). If, according to decision step 826, alarm buffer 500 does not contain dynamic patient data, then process 722 proceeds immediately to step 810.

Process 722 repeats steps 810, 812, 818, 820, 824, 826, and 828 continuously, displaying real-time physiological data to the user, until the user responds to the received alarm or until the timeout period expires because the user failed to respond to the alarm within a predetermined amount of time.

Figure 9:
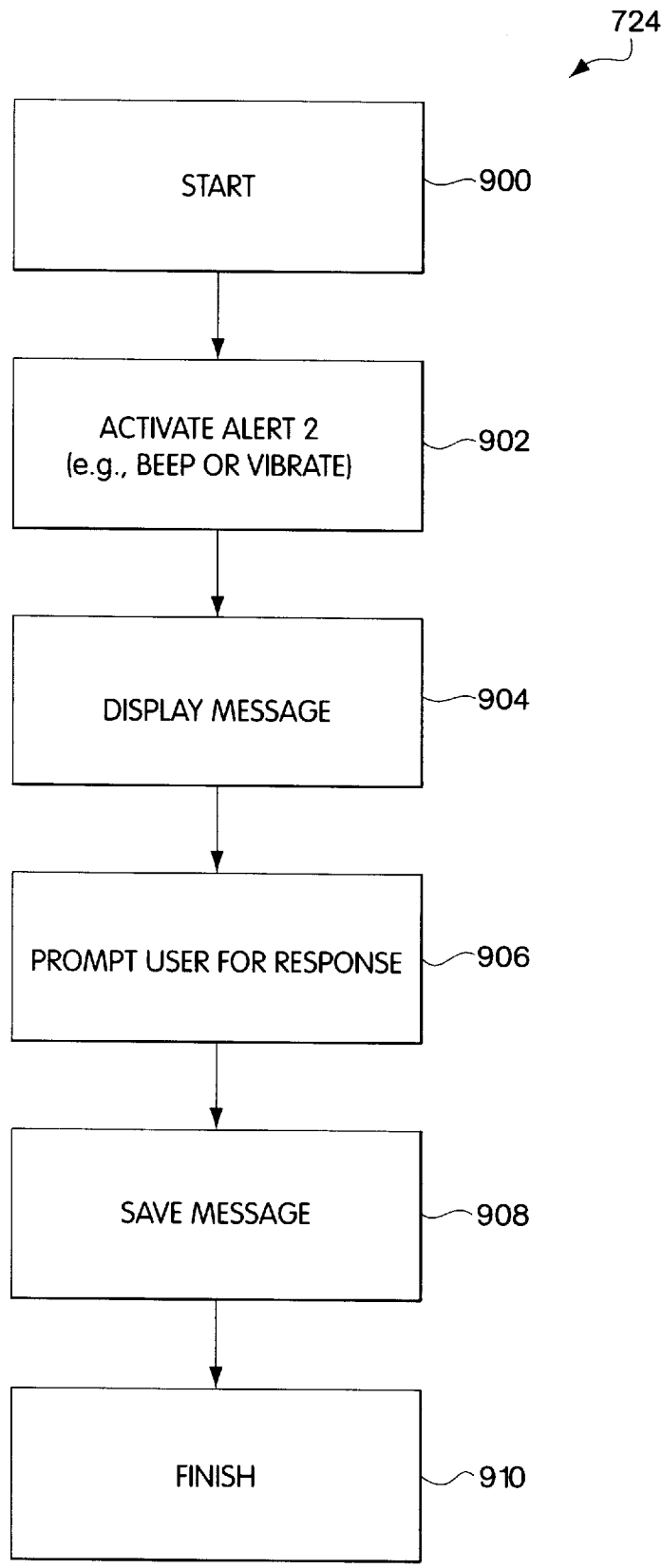
FIG. 9 shows the "process page" step shown in FIG. 7 in more detail.

FIG. 9 shows process 724 of process 614 (FIG. 7) in more detail. As shown, process 724 begins at step 900 and proceeds immediately to step 902, wherein an indication is generated and presented to the user to alert the user that a page message has been received. After step 902 is completed, process 724 proceeds to step 904.

In step 904, the received page message is displayed to the user. Process 724 then proceeds to step 906, wherein the user is prompted for a response to the page message. This prompting may be, for example, in the form of soft buttons 304A–304C shown in FIG. 3, except that the buttons may give the user the option to "return," "store," or "delete" the received page message. After step 906 is completed, process 724 proceeds to step 908.

In step 908, the page message is stored in memory so that the user may retrieve and properly respond to the message at a later time. Therefore, the user may accumulate several page messages and may review such messages when convenient. Because process 724 does not wait (in a loop) for a response for a predetermined, as is done in process 722, other incoming messages, for example, alarm messages, may be received after a page message has been received but before the user has responded to the page message. In such a situation, because the page message was saved in step 908, the user may recall it, for example, by pressing hard button 306B (FIG. 3) and scrolling though one or more saved page messages that appear on display 300. The user then may select an appropriate response to the recalled page message by using soft buttons and/or hard buttons in the manner described above. After step 908 is completed, process 724 finishes at step 910, and process 614 proceeds to step 736 (FIG. 7).

The embodiment of the handheld clinical terminal described above provides many of the capabilities and advantages of a central station, but is portable. It therefore acts as a "decentralized" central station. The described embodiment allows the distribution of alarms to only those clinicians who need to know about them, which lowers the "information overload" for all clinicians. It provides a mechanism for faster acknowledgment of alarms as well as a tracking mechanism to identify who received each alarm and how long it took clinicians to acknowledge the alarms. This information may be recorded, for example, at the central station, to maintain an electronic log of alarm-related information. Distributing the information to where the clinician is located saves the clinician work because he or she does not need to walk to the central station to review patient-specific data. The ability to view real-time data from any place on the wireless network (and not just at the patient's bedside or at the central station) increases the clinician's efficiency and effectiveness. In sum, the present invention brings the central station to the clinician instead of requiring the clinician go to the central station.

Since the described embodiment includes two-way wireless communication, clinicians may request data on a specific patient from the central station or from another device on the network. This request may be based on an alarm indication received by the clinician, or on some other "reminder" mechanism that may be automated. This ability to have information both "pushed" to the clinician as well as "pulled" by the clinician is significant. It increases the ability of the clinician to make prudent and timely medical decisions.

The ability to distribute the data directly to the clinicians in possession of handheld terminals eliminates the need to have a trained clinician located at the central station at all times. This reduces hospital costs without compromising the quality of care given to patients.

Since the device is portable, clinicians who wish to review a patient's real-time data may do so from any location. For example, a clinician may review a patient's real-time data from home, in his/her car, or in the cafeteria.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A handheld portable device for monitoring a patient, comprising:
   a receiver adapted to receive dynamic patient data, which represents a dynamically-changing physiological condition of the patient, via a wireless communication link;
   a display configured to display, based upon the dynamic patient data, a dynamically-changing representation of the physiological condition to a user; and
   an alarm exhibitor configured to provide an alarm indication, separate from the dynamically-changing representation of the physiological condition, to the user in response to receiving an alarm signal, via the wireless communication link, from a separate monitoring device, the alarm signal being generated in response to an identified anomaly in the physiological condition of the patient.

2. The portable device as claimed in claim 1, in combination with the separate monitoring device, wherein the separate monitoring device includes a primary station configured to generate the alarm signal in response to identifying the anomaly in the physiological condition of the patient, and to transmit the alarm signal to the receiver of the portable device.

3. The portable device as claimed in claim 1, wherein:
   a processor and a memory configure the alarm exhibitor to provide the alarm indication to the user, and
   instructions stored in the memory, when executed by the processor, cause the alarm exhibitor to provide the alarm indication to the user in response to the alarm signal.

4. The portable device as claimed in claim 1, wherein:
   a processor and a memory configure the display to display the representation of the physiological condition to the user, and
   instructions stored in the memory, when executed by the processor, cause the display to display the representation of the physiological condition based upon the dynamic patient data.

5. The portable device as claimed in claim 1, wherein:
   the device further comprises a speaker,
   the receiver is adapted to receive audio messages via the wireless communication link, and
   the speaker is configured to provide the audio messages to the user.

6. The portable device as claimed in claim 1, wherein:
   the receiver is adapted to receive page messages via the wireless communication link, and
   the display is configured to provide the page messages to the user, the display being configured such that alarm signals are given priority over page messages.

7. The portable device as claimed in claim 1, wherein the display is configured to display, based upon the dynamic patient data, a moving waveform representing the physiological condition of the patient.

8. The portable device as claimed in claim 1, wherein the receiver is adapted to receive a Java applett, via the wireless communication link, to which the dynamic patient data may be streamed.

9. The portable device as claimed in claim 1, wherein the display is configured to display based upon the dynamic patient data, a real-time representation of the physiological condition to the user.

10. The portable device as claimed in claim 1, further comprising:
    at least first and second buttons, the at least first and second buttons having identification information associated therewith indicating that activation of the at least first and second buttons will cause respective at least first and second predefined responses to the alarm condition to be transmitted; and
    a transmitter adapted to communicate, via the wireless communication link, with a primary station to permit the user to communicate one of the at least first and second predefined responses to the alarm indication to the primary station by activating a corresponding one of the at least first and second buttons.

11. A portable device for monitoring a physiological condition of a patient, comprising:
    a receiver adapted to receive a signal, which represents the physiological condition of the patient, via a wireless communication link;
    a display configured to display, based upon the signal, a representation of the physiological condition to a user;
    an alarm exhibitor configured to provide an alarm indication to the user in response to an identified anomaly in the physiological condition of the patient;
    at least first and second buttons, the at least first and second buttons having identification information associated therewith indicating that activation of the at least first and second buttons will cause respective at least first and second predefined responses to the alarm condition to be transmitted; and
    a transmitter adapted to communicate, via the wireless communication link, with a primary station to permit the user to communicate one of the at least first and second predefined responses to the alarm indication to the primary station by activating a corresponding one of the at least first and second buttons.

12. The portable device as claimed in claim 11, wherein the alarm exhibitor is configured to exhibit the alarm indication in response to an alarm signal received, via the wireless communication link, from the primary station.

13. The portable device as claimed in claim 12, wherein:
    a processor and a memory configure the alarm exhibitor to provide the alarm indication to the user; and
    instructions stored in the memory, when executed by the processor, cause the alarm exhibitor to provide the alarm indication to the user in response to the alarm signal.

14. The portable device as claimed in claim 11, wherein:
    a processor and a memory configure the display to display the representation of the physiological condition to the user, and instructions stored in the memory, when executed by the processor, cause the display to display the representation of the physiological condition based upon the signal.

15. The portable device as claimed in claim 11, wherein:
the device further comprises a speaker,
the receiver is adapted to receive audio messages via the wireless communication link, and
the speaker is configured to provide the audio messages to the user.

16. The portable device as claimed in claim 11, wherein:
the receiver is adapted to receive page messages via the wireless communication link, and
the display is configured to provide the page messages to the user, the display being configured such that alarm signals are given priority over page messages.

17. The portable device as claimed in claim 11, wherein the display is configured to display, based upon the signal, a moving waveform representing the physiological condition of the patient.

18. The portable device as claimed in claim 11, wherein the receiver is adapted to receive a Java applett, via the wireless communication link, to which the signal may be streamed.

19. The portable device as claimed in claim 11, wherein the display is configured to display the identification information associated with the at least first and second buttons.

20. The portable device as claimed in claim 11, wherein:
the receiver is adapted to receive dynamic patient data, which represents a dynamically-hanging physiological condition of the patient, via the wireless communication link; and
the display is configured to display, based upon the dynamic patient data, a dynamically-changing representation of the physiological condition to the user.

21. The portable device as claimed in claim 11, wherein the display is configured to display the at least first and second buttons.

22. The portable device as claimed in claim 21, wherein the display is configured to display the identification information associated with the at least first and second buttons.

23. A method for monitoring a patient, comprising the steps of:
using a handheld portable station to receive dynamic patient data, which represents a dynamically-changing physiological condition of the patient, via a wireless communication link;
using the portable station to display, based upon the dynamic patient data, a dynamically-changing representation of the physiological condition to a user;
using a device other than the portable station to identify an anomaly in the physiological condition of the patient; and
using the portable station to exhibit an alarm indication, separate from the dynamically-changing representation of the physiological condition, to the user in response to the device other than the portable station identifying the anomaly in the physiological condition of the patient.

24. The method of claim 23, wherein the step of using the portable station to display the dynamically-changing representation of the physiological condition to the user includes the step of using the portable station to display a real-time representation of the physiological condition to the user.

25. The method as claimed in claim 23, further comprising the steps of:
after the portable station exhibits the alarm indication, activating one of at least two buttons on the portable station;
in response to a first one of the at least two buttons being activated, using the portable station to transmit a first predefined response to the alarm indication, via the wireless communication link, to the device other than the portable station; and
in response to a second one of the at least two buttons being activated, using the portable station to transmit a second predefined response to the alarm indication, via the wireless communication link to the device other than the portable station.

26. The method according to claim 23, further including a step of:
in response to the device other than the portable device identifying the anomaly in the physiological condition of the patient, transmitting an alarm signal from the device other than the primary device to the portable device via the wireless communication link.

27. A method for monitoring a patient, comprising the steps of:
using a portable station to receive a signal, which represents a physiological condition of the patient, via a wireless communication link;
using the portable station to display, based upon the signal, a representation of the physiological condition to a user;
using the portable station to exhibit an alarm indication to the user in response to an identified anomaly in the physiological condition of the patient;
after the portable station exhibits the alarm indication, activating one of at least two buttons on the portable station;
in response to a first one of the at least two buttons being activated, using the portable station to transmit a first predefined response to the alarm indication, via the wireless communication link, to a primary station; and
in response to a second one of the at least two buttons being activated, using the portable station to transmit a second predefined response to the alarm indication, via the wireless communication link, to the primary station.

28. The method according to claim 27, further comprising the step of using a device other than the portable station to identify the anomaly in the physiological condition of the patient.

29. The method according to claim 27, wherein:
the step of using the portable station to receive the signal includes a step of using the portable station to receive dynamic patient data, which represents a dynamically-changing physiological condition of the patient, via the wireless communication link; and
the step of using the portable station to display the representation of the physiological condition to the user includes a step of using the portable station to display, based upon the dynamic patient data, a dynamically-changing representation of the physiological condition to the user.

30. The method as claimed in claim 27, further including the step of displaying the at least two buttons on a display of the portable device.

31. The method as claimed in claim 30, further including the step of displaying information on the display indicating that activation of the first and second buttons, respectively, will cause the first and second predetermined responses to the alarm indication to be transmitted to the primary station.

32. The method as claimed in claim 27, further including the step of displaying information on a display of the primary station indicating that activation of the first and second buttons, respectively, will cause the first and second predetermined responses to the alarm indication to be transmitted to the primary station.

* * * * *